(12) United States Patent
Lee et al.

(10) Patent No.: US 11,345,688 B2
(45) Date of Patent: May 31, 2022

(54) COMPOUND, PREPARING METHOD THEREFOR, AND ORGANIC LIGHT EMITTING ELEMENT COMPRISING SAME

(71) Applicant: DAEGU GYEONGBUK INSTITUTE OF SCIENCE AND TECHNOLOGY, Daegu (KR)

(72) Inventors: Youn Gu Lee, Daegu (KR); Hong Gi Kim, Changwon-si (KR); Seok Hoon Jang, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 372 days.

(21) Appl. No.: 16/482,596

(22) PCT Filed: Jan. 22, 2018

(86) PCT No.: PCT/KR2018/000939
§ 371 (c)(1),
(2) Date: Jul. 31, 2019

(87) PCT Pub. No.: WO2018/143591
PCT Pub. Date: Aug. 9, 2018

(65) Prior Publication Data
US 2019/0359602 A1    Nov. 28, 2019

(30) Foreign Application Priority Data
Jan. 31, 2017    (KR) .................. 10-2017-0014073

(51) Int. Cl.
*C07D 405/14* (2006.01)
*H01L 51/00* (2006.01)
*H01L 51/50* (2006.01)

(52) U.S. Cl.
CPC ........ *C07D 405/14* (2013.01); *H01L 51/0067* (2013.01); *H01L 51/5056* (2013.01);
(Continued)

(58) Field of Classification Search
None
See application file for complete search history.

(56) References Cited

U.S. PATENT DOCUMENTS

2016/0372524 A1* 12/2016 Yun ..................... H01L 51/5092
2017/0025618 A1    1/2017 Zheng et al.

FOREIGN PATENT DOCUMENTS

KR    10-2013-0036048 A    4/2013
KR    10-2016-0006633 A    1/2016
(Continued)

OTHER PUBLICATIONS

Fan et al. "Dibenzothiophene Sulfone-Based Phosphine Oxide Electron Transporters with Unique Asymmetry for High-Efficiency Blue Thermally Activated Delayed Fluorescence Diodes" ACS Appl. Mater & Interfaces, 2016, 8, 27383-27393. (Year: 2016).*

*Primary Examiner* — Robert S Loewe
(74) *Attorney, Agent, or Firm* — Harness, Dickey & Pierce, P.L.C.

(57) ABSTRACT

The compound is represented by Formula 1. In Formula 1, X is O or S, and $R^1$ and $R^2$ are independently selected from the group consisting of aryl, heteroaryl and —P(O)—$R^3R^4$, where the aryl, heteroaryl and —P(O)—$R^3R^4$ are substituted or unsubstituted with 1 to 4 substituents selected from the group consisting of ($C_1$-$C_4$)alkyl, ($C_1$-$C_4$)alkoxy, aryl and heteroaryl. The "aryl" means a group consisting of 6 to 10 cyclic rings, and the "heteroaryl" means a group consisting of 5 to 14 cyclic rings having 1 to 4 heteroatoms selected (Continued)

from oxygen, sulfur and nitrogen (including quaternary nitrogen). $R^3$ and $R^4$ are independently selected from aryl or heteroaryl.

9 Claims, 7 Drawing Sheets

(52) U.S. Cl.
CPC ...... *H01L 51/5072* (2013.01); *H01L 51/5092* (2013.01); *H01L 51/5096* (2013.01)

(56) References Cited

FOREIGN PATENT DOCUMENTS

| KR | 10-2016-0142909 A | 12/2016 |
| KR | 10-2016-0150184 A | 12/2016 |

\* cited by examiner

COMPOUND, PREPARING METHOD THEREFOR, AND ORGANIC LIGHT EMITTING ELEMENT COMPRISING SAME

TECHNICAL FIELD

Various embodiments of the present disclosure relate to a compound, a preparation method thereof and an organic light emitting device comprising the same.

BACKGROUND ART

Recently, importance of flat panel display (FPD) has been increasing along with development of multimedia. In response thereto, various displays, such as a liquid crystal display (LCD), plasma display panel (PDP), field emission display (FED) and organic light-emitting diode (OLED), have been commercialized.

An OLED not only enables formation of a device on a flexible substrate such as plastic, but also can be operated at a voltage of as low as 10 V or less compared to a plasma display or an inorganic electroluminescence display. The OLED is also advantageous in having relatively low power consumption and excellent color display. Further, the OLED can exhibit three colors of red, green and blue, and thus has drawn attention as a next generation display device that expresses full colors.

Meanwhile, in order to commercialize a highly efficient long-life OLED, it is essential to develop not only phosphorescence or fluorescence and luminescence materials, which determine luminescence characteristics, but also electron transport layer materials, which improve properties of the OLEDs by effectively transporting electrons injected from a cathode to an emission layer.

In particular, it is essential to develop a novel electron transport layer material for OLEDs, which can secure high triplet energy and electron mobility, facilitate hole blocking and electron injection while optimizing thermal stability, in order to commercialize the OLED having high efficiency.

However, the electron transport layer materials, which have so far been developed, are known to have not only lower triplet energy than blue phosphorescent dopant materials but also poor electron mobility, thereby significantly reducing efficiency of the OLEDs.

Additionally, the existing electron transport layer materials have a low glass transition temperature (Tg) and thus have significantly poor thermal stability due to a limitation of a molecular structure for improving triplet energy. Consequently, the poor thermal stability of the electron transport layer materials significantly reduce life expectancy of the OLEDs, which serves to have a fundamental problem of being unable to be applied to commercialization.

SUMMARY OF INVENTION

Technical Problem

In various embodiments of the present disclosure, a compound capable of securing high triplet energy and electron mobility, facilitating hole blocking and electron injection, and optimizing thermal stability, a method for preparing the same, and an organic light-emitting diode (OLED) comprising the same may be provided.

Solution to Problem

A compound according to various embodiments of the present disclosure is represented by Formula 1 below:

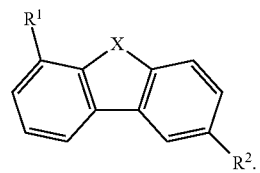

[Formula 1]

In Formula 1, X is O or S, $R^1$ and $R^2$ are independently selected from the group consisting of aryl, heteroaryl and —P(O)—$R^3R^4$. The aryl, heteroaryl and —P(O)—$R^3R^4$ are substituted or unsubstituted with 1 to 4 substituents selected from the group consisting of ($C_1$-$C_4$)alkyl, ($C_1$-$C_4$)alkoxy, aryl and heteroaryl. The "aryl" means a group consisting of 6 to 10 cyclic rings, and the "heteroaryl" means a group consisting of 5 to 14 cyclic rings having 1 to 4 heteroatoms selected from oxygen, sulfur and nitrogen (including quaternary nitrogen). $R^3$ and $R^4$ are independently selected from aryl or heteroaryl.

Advantageous Effects of Invention

In various embodiments of the present disclosure, a compound capable of securing high triplet energy and electron mobility, facilitating hole blocking, and electron injection and optimizing thermal stability, a method for preparing the same, and an organic light-emitting diode (OLED) comprising the same may be provided.

DESCRIPTION OF EMBODIMENTS

Figure 1:
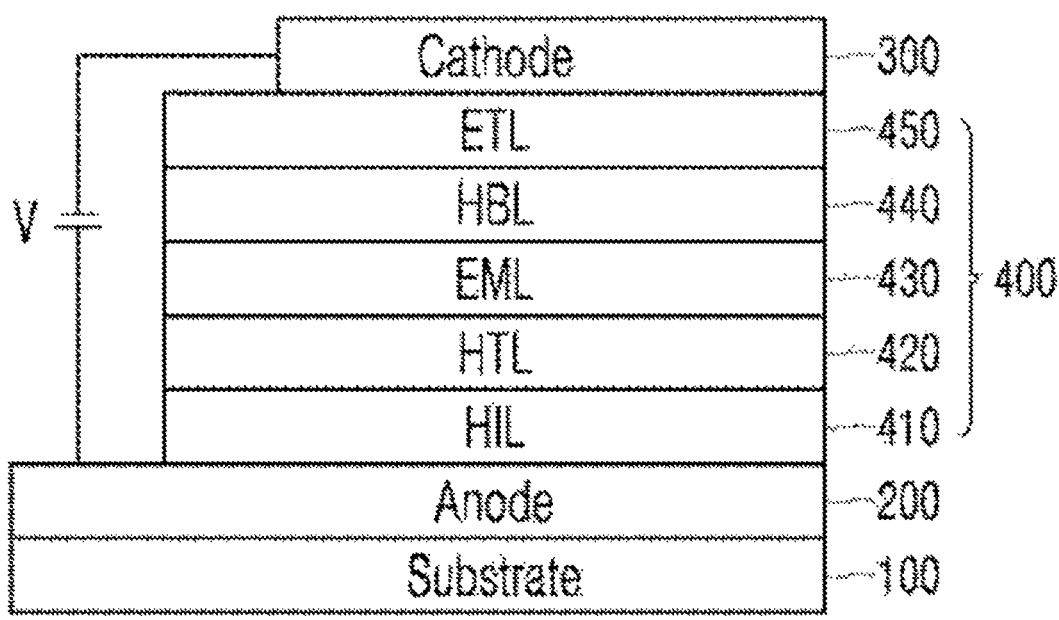
FIG. 1 is a schematic cross-sectional view of the OLED according to various embodiments.

Hereinbelow, various embodiments of the present disclosure will be described with reference to the accompanying drawings. However, the embodiments and the terminologies used therein should not be limited to a specific embodiment and should be construed as including various modifications, equivalent devices and methods, and/or alternatives.

Hereinbelow, the embodiments of the present disclosure will be described as follows with reference to the accompanying drawings.

Various embodiments of the present disclosure relate to a compound represented by Formula 1 below:

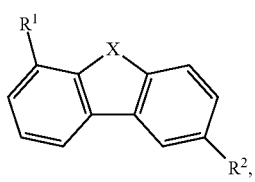

[Formula 1]

wherein X is O or S, $R^1$ and $R^2$ are independently selected from the group consisting of aryl, heteroaryl and —P(O)—$R^3R^4$.

The aryl, heteroaryl and —P(O)—$R^3R^4$ are substituted or unsubstituted with 1 to 4 substituents selected from the group consisting of $(C_1-C_4)$alkyl, $(C_1-C_4)$alkoxy, aryl and heteroaryl.

The term "aryl" means a group consisting of 6 to 10 cyclic rings, and the term "heteroaryl" means a group consisting of 5 to 14 cyclic rings having 1 to 4 heteroatoms selected from oxygen, sulfur and nitrogen (including quaternary nitrogen).

$R^3$ and $R^4$ are independently selected from aryl or heteroaryl.

Specifically, the R1 and R2 are independently selected from the group consisting of (1) pyridine, (2) pyrimidine, (3) phenylpyrimidine, (4) diphenyltriazine, (5) dipyridylbenzene, (6) phenyltetrazine, (7) triphenyldiazole, (8) diphenylphosphine oxide, (9) diphenyltriazole, (10) diphenyloxazole, (11) diphenylthiazole, (12) phenyloxadiazole and (13) phenylthiadiazole. Such substituents have the following formulae:

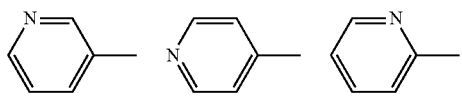

(1) pyrine

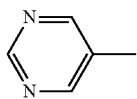

(2) pyrimidine

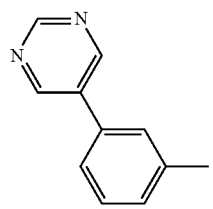

(3) phenylpyrimidine

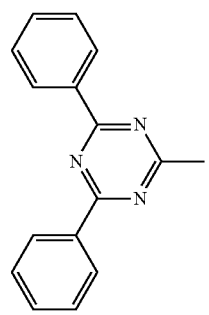

(4) diphenyltriazine

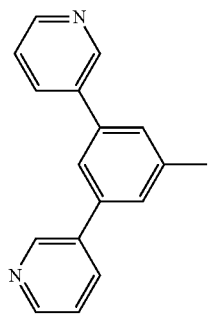

(5) dipyridylbenzene

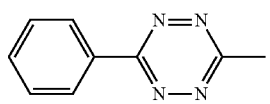

(6) phenyltetrazine

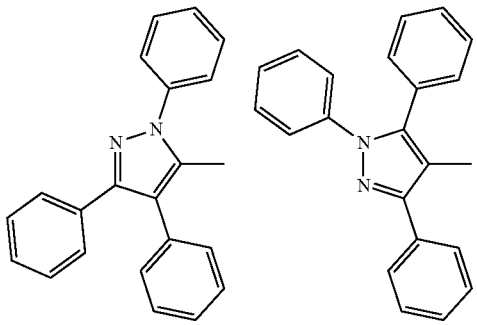

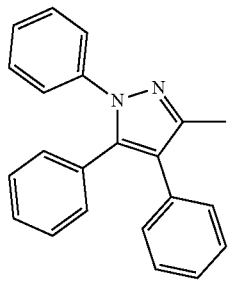

(7) triphenyldiazole

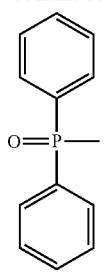
(8) diphenylphosphine oxide
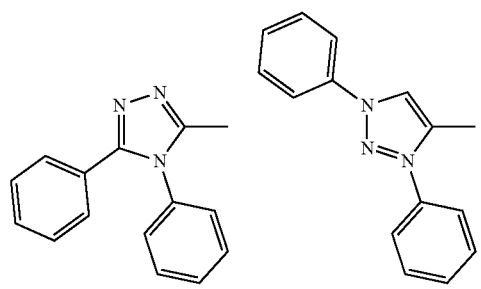
(9) diphenyltriazole
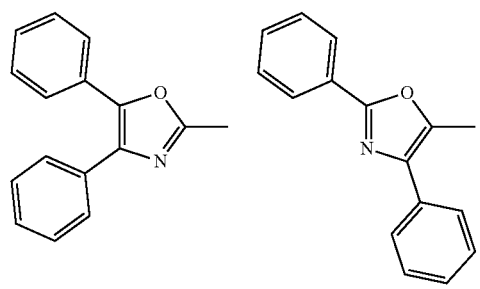
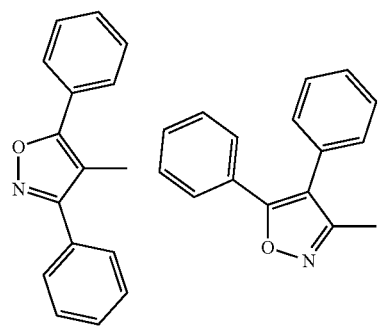
(10) diphenyloxazole
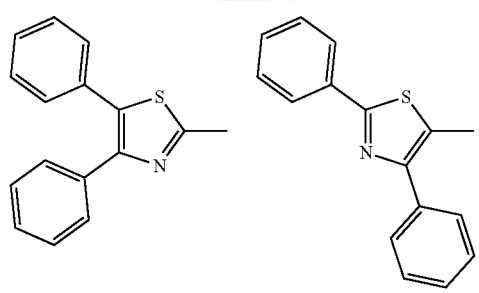
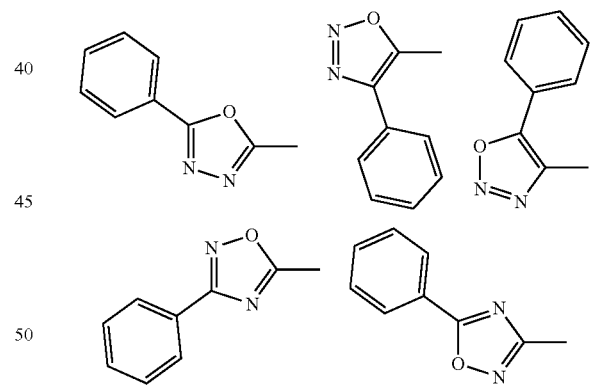
(11) diphenylthiazole
(12) phenyloxadiazole
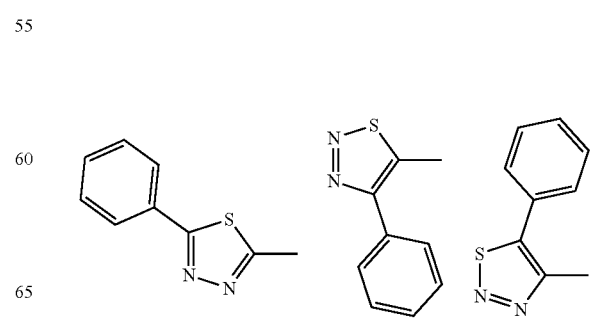

-continued

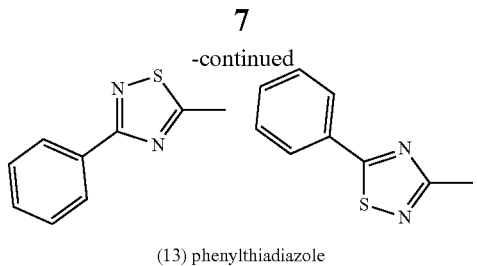

(13) phenylthiadiazole

According to various embodiments, the compound represented by Formula 1 above may include a compound represented by Formula 2 below:

[Formula 2]

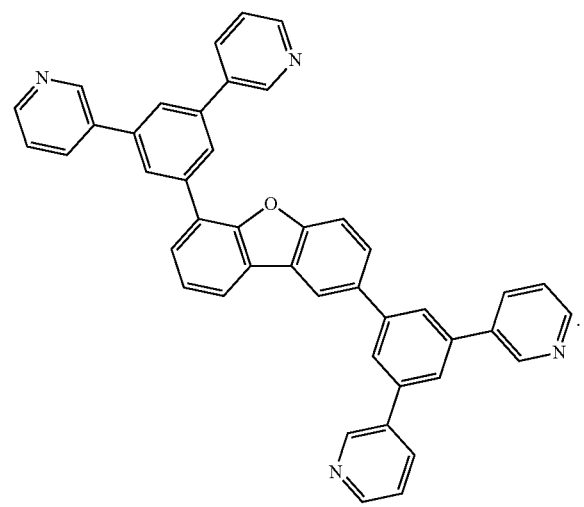

That is, the compound according to various embodiments may have a structure in which X is O, $R^1$ and $R^2$ are aryl, where the aryls are substituted with heteroaryls. Or, the compound according to various embodiments may have a structure in which C2 and C6 of dibenzofuran are substituted with dipyridylbenzene.

According to various embodiments, the compound represented by Formula 1 may include a compound represented by Formula 3 below:

[Formula 3]

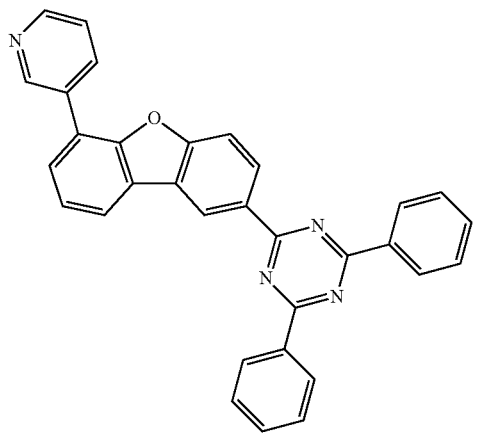

That is, the compound according to various embodiments may have a structure in which X is O, $R^1$ and $R^2$ are heteroaryl, where the heteroaryls may be unsubstituted or substituted with aryls. Or, the compound according to various embodiments may have a structure in which C2 and C6 of dibenzofuran are substituted with pyridine and diphenyltriazole, respectively.

Meanwhile, the embodiments are not limited thereto. The compound according to various embodiments may have a structure in which C2 and C6 of dibenzothiophene are substituted with various substituents.

Embodiments

The compound according to various embodiments can be synthesized through the preparation methods below.

Specific embodiments are as follows.

EXAMPLES

Example 1

Synthesis of Compound 2 of Formula 2

The compound of Formula 2 was synthesized through the following steps:

Step 1: Synthesis of Intermediate Product (Compound 3-A)

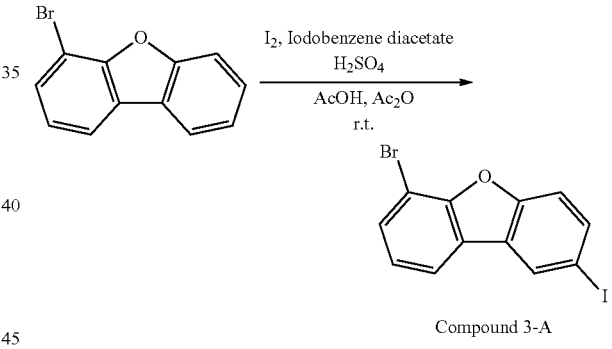

Compound 3-A 4-bromodibenzofuran (2 g, 8.1 mmol), iodobenzene-diacetate (1.3 g, 4.0 mmol) and iodine (1.03 g, 4.0 mmol) were suspended in 10 mL of acetic anhydride and 10 mL of acetic acid. After adding a small amount of sulfuric acid, the mixture was stirred at room temperature under nitrogen flow for 36 hours. Upon completion of the reaction, the organic layer was extracted with dichloromethane. The solution was dried using anhydrous sodium sulfate. After vacuum distillation, the solution was columned and recrystallized with hexane to obtain compound 3-A (1.8 g, yield: 60%).

Step 2: Synthesis of Intermediate Product (Compound 3-B)

-continued

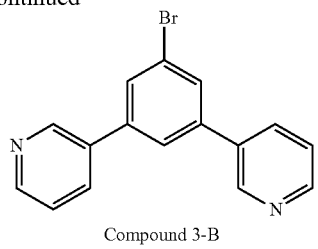

Compound 3-B

Step 4: Synthesis of Final Product (Compound of Formula 2)

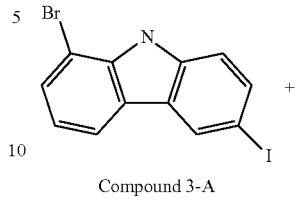

Compound 3-A

Pyridine-3-boronic acid (4.1 g, 33.4 mmol), 1,3,5-tribromobenzene (5 g, 15.9 mmol) and sodium carbonate (3.4 g, 31.8 mmol), tetrakis(triphenylphosphine)palladium 0.92 g, 0.79 mmol) were suspended in 50 mL of dioxane and 25 mL of distilled water. The mixture was refluxed under nitrogen flow for 12 hours. Upon completion of the reaction, the organic layer was extracted with dichloromethane. The solution was dried using anhydrous sodium sulfate. After vacuum distillation, the solution was columned with ethyl acetate to obtain compound 3-B (2 g, yield: 40%).

1H NMR (400 MHz, CDCl3) δ (ppm)=8.88-8.87 (d, 2H), 8.67-8.65 (dd, 2H), 7.92-7.89 (dt, 2H), 7.76 (d, 2H), 7.69-7.68 (t, 1H), 7.43-7.40 (dd, 2H)

Step 3: Synthesis of Intermediate Product (Compound 3-C)

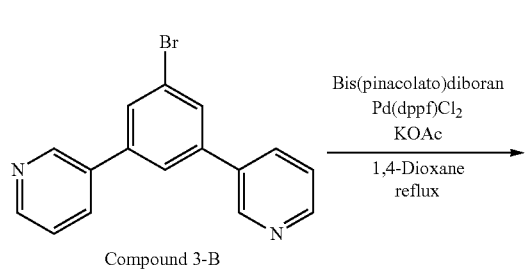

Compound 3-B

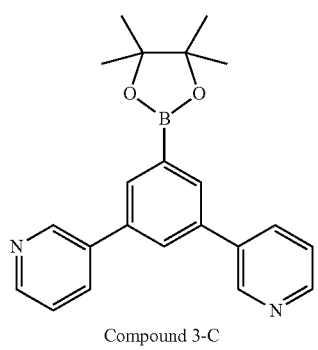

Compound 3-C

Compound 3-B (5 g, 16.1 mmol), bis(pinacolato)diboron (5.3 g, 20.9 mmol), potassium acetate (4.7 g, 48.2 mmol), [1,1'-bis(diphenylphosphino)ferrocene]dichloropalladium dichloromethane (0.66 g, 0.80 mmol) were suspended in 100 mL of dioxane. The mixture was refluxed under nitrogen flow for 12 hours. Upon completion of the reaction, the organic layer was extracted with dichloromethane. The solution was dried using anhydrous sodium sulfate. After vacuum distillation, the solution was columned with ethyl acetate to obtain compound 3-C (4.7 g, yield: 82%).

1H NMR (400 MHz, CDCl3) δ (ppm)=8.94-8.93 (dd, 2H), 8.64-8.62 (dd, 2H), 8.07 (d, 2H), 7.99-7.96 (dt, 2H), 7.87-7.86 (t, 1H), 7.41-7.38 (dd, 2H), 1.39 (s, 12H)

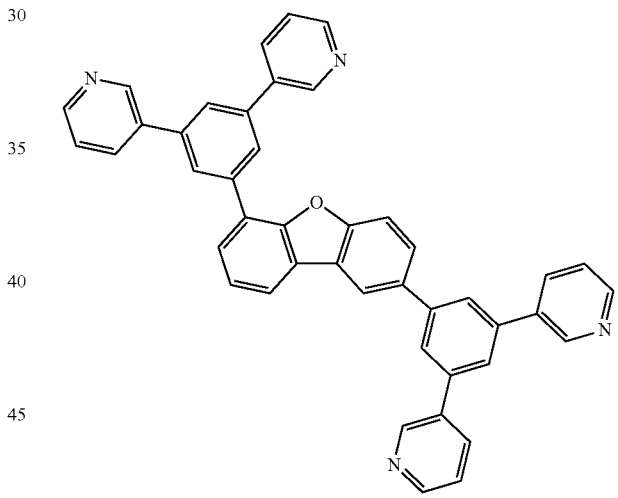

Compound 3-A (2 g, 5.4 mmol), compound 3-C (4.4 g, 12.3 mmol), potassium phosphate (3.4 g, 16.1 mmol), tris(dibenzylidyneacetone)dipalladium (0.25 g, 0.27 mmol) and SPhos (0.22 g, 0.54 mmol) were suspended in 100 mL of dioxane and 50 mL of distilled water. The mixture was refluxed under nitrogen flow for 24 hours. Upon completion of the reaction, the organic layer was extracted with dichloromethane. The solution was dried using anhydrous sodium sulfate. After vacuum distillation, the solution was columned with methanol and dichloromethane at a ratio of 1:19 to obtain compound 3 (1 g, 30%).

1H NMR (400 MHz, CDCl3) δ (ppm)=9.04-9.03 (dd, 2H), 9.01-9.00 (dd, 2H), 8.69-8.67 (m, 4H), 8.31-8.30 (d, 1H), 8.17-8.16 (d, 2H), 8.10-8.08 (dd, 1H), 8.07-8.02 (m, 4H), 7.93-7.92 (d, 2H), 7.85-7.84 (t, 1H), 7.84-7.81 (dd, 1H), 7.78-7.77 (t, 1H), 7.76-7.72 (m, 2H), 7.56-7.52 (t, 1H), 7.48-7.43 (m, 4H)

Comparative Example 1

TmPyPB, a compound having the following formula:

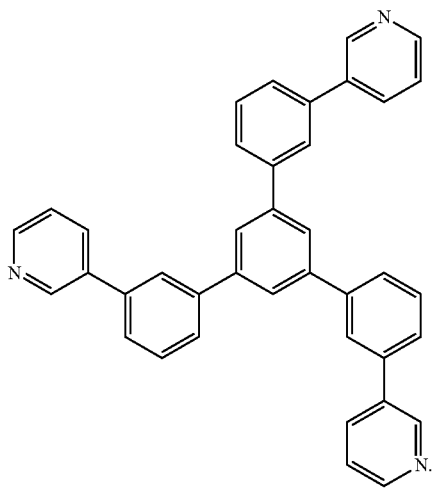 [SMILES: c1cncc(-c2cccc(-c3cc(-c4cccc(-c5cccnc5)c4)cc(-c4cccc(-c5cccnc5)c4)c3)c2)c1]

Comparative Example 2

TPBI, a compound having the following formula:

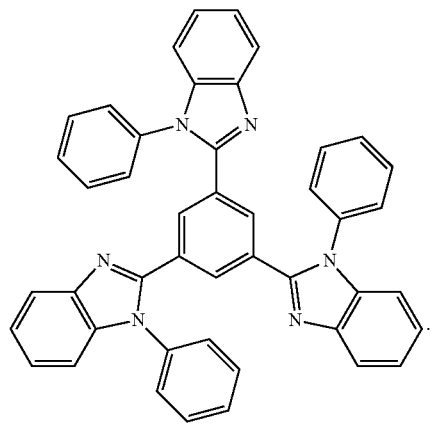 [SMILES: c1ccc(-n2c(-c3cc(-c4nc5ccccc5n4-c4ccccc4)cc(-c4nc5ccccc5n4-c4ccccc4)c3)nc3ccccc32)cc1]

Table 1 below shows a comparison of properties of the compound synthesized according to Example 1, Comparative Examples 1 and 2.

TABLE 1

| Compound | Tg(° C.) | $E_T$ (eV) |
|---|---|---|
| Compound synthesized according to Example 1 (compound of Formula 2) | 134 | 2.75 |
| Comparative Example 1 | 79 | 2.75 |
| Comparative Example 2 | 129 | 2.69 |

According to Table 1, a glass transition temperature (Tg) of the compound synthesized according to Example 1 was 134° C., which is significantly higher than those of Comparative Examples 1 and 2. Further, triplet energy ($E_T$) of the compound synthesized according to Example 1 was higher than that of Comparative Example 2 and similar to that of Comparative Example 1.

Accordingly, the compound synthesized according to Example 1 can have thermal stability through the high glass transition temperature. When applied to an organic thin film layer of an OLED, the compound synthesized according to Example 1 can secure a highly efficient and long-life OLED through high triplet energy.

Example 2

Synthesis of Compound of Formula 3

The compound of Formula 3 was synthesized through the following steps.

Step 1: Synthesis of Intermediate Product (Compound 4-A)

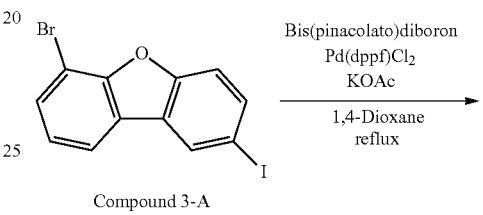

Compound 3-A

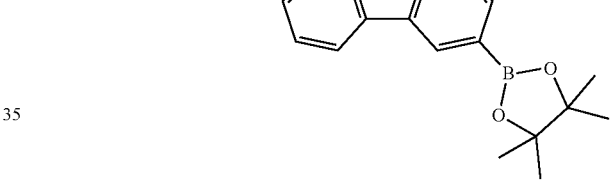

Compound 4-A

Compound 3-A (5 g, 13.4 mmol), bis(pinacolato) diboron (4.1 g, 16.1 mmol), potassium acetate (3.95 g, 40.2 mmol), [1,1'-bis(diphenylphosphino)ferrocene] dichloropalladium dichloromethane (0.55 g, 0.70 mmol) were suspended in 150 mL of dioxane. The mixture was refluxed under nitrogen flow for 12 hours. Upon completion of the reaction, the organic layer was extracted with dichloromethane. The solution was dried using anhydrous sodium sulfate. After vacuum distillation, the solution was columned with hexane and dichloromethane at a ratio of 4:1 to obtain compound 4-A (3 g, yield: 60%).

1H NMR (400 MHz, CDCl3) δ (ppm)=8.43 (s, 1H), 7.98-7.95 (dd, 1H), 7.91-7.89 (dd, 1H), 7.66-7.64 (dd, 1H), 7.62-7.60 (dd, 1H), 7.25-7.21 (t, 1H), 1.40 (s, 12H)

Step 2: Synthesis of Intermediate Product (Compound 4-B)

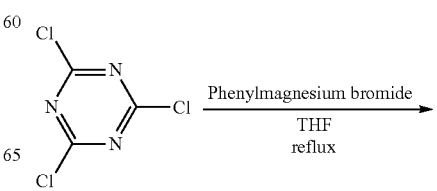

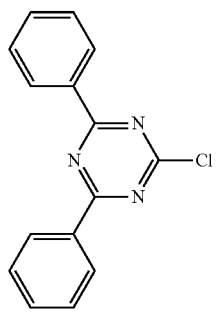

Compound 4-B

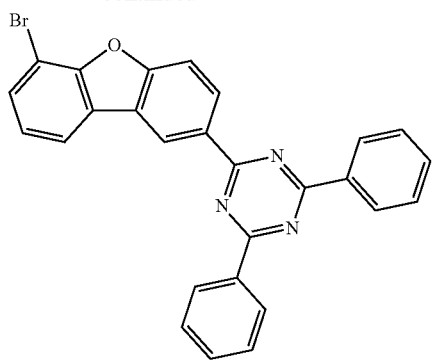

Compound 4-C

Magnesium (2.57 g, 105.7 mmol) and iodine (0.54 g, 2.1 mmol) were added to 30 mL of tetrahydrofuran and stirred. A solution in which bromobenzene (11.1 g, 70.5 mmol) was dissolved in 30 mL of tetrahydrofuran was slowly added dropwise to the above solution.

A solution in which 1,3,5-trichlorotriazine (5 g, 27.1 mmol) was dissolved in 30 mL of tetrahydrofuran was slowly added dropwise to the above solution at 0° C. The mixture was refluxed for 12 hours. Upon completion of the reaction, the organic layer was extracted with dichloromethane. The solution was dried using anhydrous sodium sulfate. After vacuum distillation, the solution was columned with hexane and dichloromethane at a ratio of 4:1 to obtain compound 4-B (4 g, yield: 55%).

1H NMR (400 MHz, CDCl3) δ (ppm)=8.65-8.62 (m, 4H), 7.66-7.62 (m, 2H), 7.58-7.54 (m, 4H)

Step 3: Synthesis of Intermediate Product (Compound 4-C)

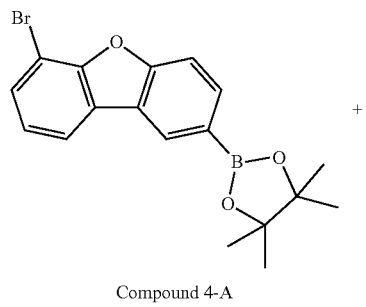

Compound 4-A

+

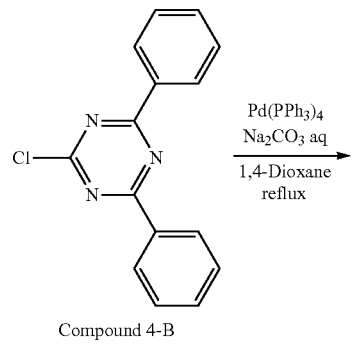

Compound 4-B $\xrightarrow{\text{Pd(PPh}_3)_4 \\ \text{Na}_2\text{CO}_3 \text{ aq} \\ \text{1,4-Dioxane} \\ \text{reflux}}$ Compound 4-A (4 g, 10.7 mmol), compound 4-B (3.4 g, 12.9 mmol), sodium carbonate (2.3 g, 21.4 mmol), tetrakis (triphenylphosphine)palladium (0.62 g, 0.54 mmol) were suspended in 100 mL of dioxane and 50 mL of distilled water. The mixture was refluxed under nitrogen flow for 12 hours. Upon completion of the reaction, the organic layer was extracted with dichloromethane. The solution was dried using anhydrous sodium sulfate. After vacuum distillation, the solution was recrystallized with hexane to obtain compound 4-C (3 g, yield: 58%).

1H NMR (400 MHz, CDCl3) δ (ppm)=9.35 (dd, 1H), 9.00-8.98 (dd, 1H), 8.82-8.79 (m, 4H), 8.11-8.09 (dd, 1H), 7.83-7.80 (dd, 1H), 7.69-7.67 (dd, 1H), 7.64-7.58 (m, 6H), 7.33-7.30 (t, 1H)

Step 4: Synthesis of Final Product (Compound of Formula 3)

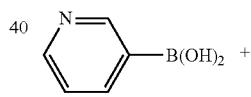

+

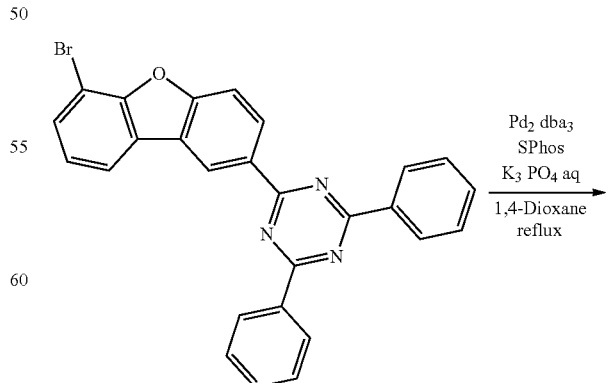

Compound 4-C $\xrightarrow{\text{Pd}_2\text{ dba}_3 \\ \text{SPhos} \\ \text{K}_3\text{PO}_4 \text{ aq} \\ \text{1,4-Dioxane} \\ \text{reflux}}$ -continued

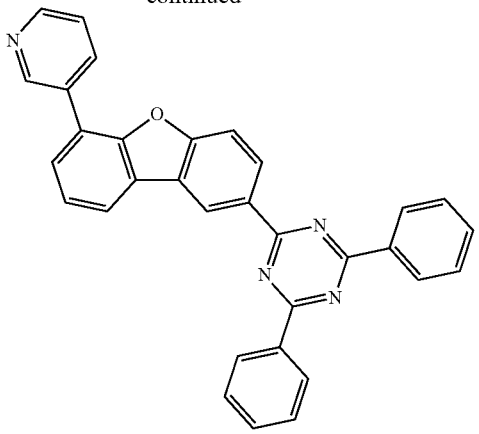

Compound 4-C (3 g, 6.3 mmol), pyridine-3-boronic acid (0.93 g, 7.5 mmol), potassium phosphate (4.0 g, 18.8 mmol), tris(dibenzylidyneacetone)dipalladium (0.29 g, 0.31 mmol) and SPhos (0.26 g, 0.63 mmol) were suspended in 100 mL of dioxane and 50 mL of distilled water. The mixture was refluxed under nitrogen flow for 36 hours. Upon completion of the reaction, the organic layer was extracted with dichloromethane. The solution was dried using anhydrous sodium sulfate. After vacuum distillation, the solution was columned with hexane and ethyl acetate at a ratio of 1:1 to obtain compound 4 (1.5 g, yield: 50%).

1H NMR (400 MHz, CDCl3) δ (ppm)=9.41 (d, 1H), 9.18 (d 1H), 9.00-8.97 (dd, 1H), 8.83-8.81 (m, 4H), 8.71-8.69 (1H), 8.28-8.25 (dt, 1H), 8.21-8.19 (dd, 1H), 7.77-7.75 (d, 1H), 7.68-7.66 (dd, 1H), 7.65-7.59 (m, 6H), 7.57-7.53 (t, 1H), 7.51-7.48 (dd, 1H)

The compounds according to various embodiments may be used as a material of an organic thin film layer of an OLED. Hereinbelow, the OLED will be described with reference to FIG. 1.

FIG. 1 is a schematic cross-sectional view of the OLED according to various embodiments.

As illustrated in FIG. 1, the OLED may include a substrate 100, an anode 200 disposed on the substrate 100, an organic thin film layer 400 and a cathode 300. The OLED may be a phosphorescent OLED or a fluorescent OLED.

The organic thin film layer 400 may include a hole injection layer (HIL) 410, a hole transport layer (HTL) 420, an emission layer (EML) 430, a hole blocking layer (HBL) 440 an electron transport layer (ETL) 450, or the like. Meanwhile, although not illustrated in the drawing, the organic thin film layer 400 may further include an electron injection layer (EIL) and an electron blocking layer (EBL). Further, according to various embodiments, the HBL 440 can block holes and transport electrons simultaneously.

The anode 200 and the cathode 300 may be formed of a metal, a metal oxide or a conductive polymer.

Any one of the organic thin film layer 400 may include the compound of Formula 1 previously described. Preferably, the ETL or the HBL 440 may include the compound of Formula 1. When the compound of Formula 1 is applied to the ETL 450 or HBL 440 of the OLED, high triplet energy and electron mobility can be secured, and hole blocking and electron injection may be facilitated while thermal stability is optimized.

Figure 2:
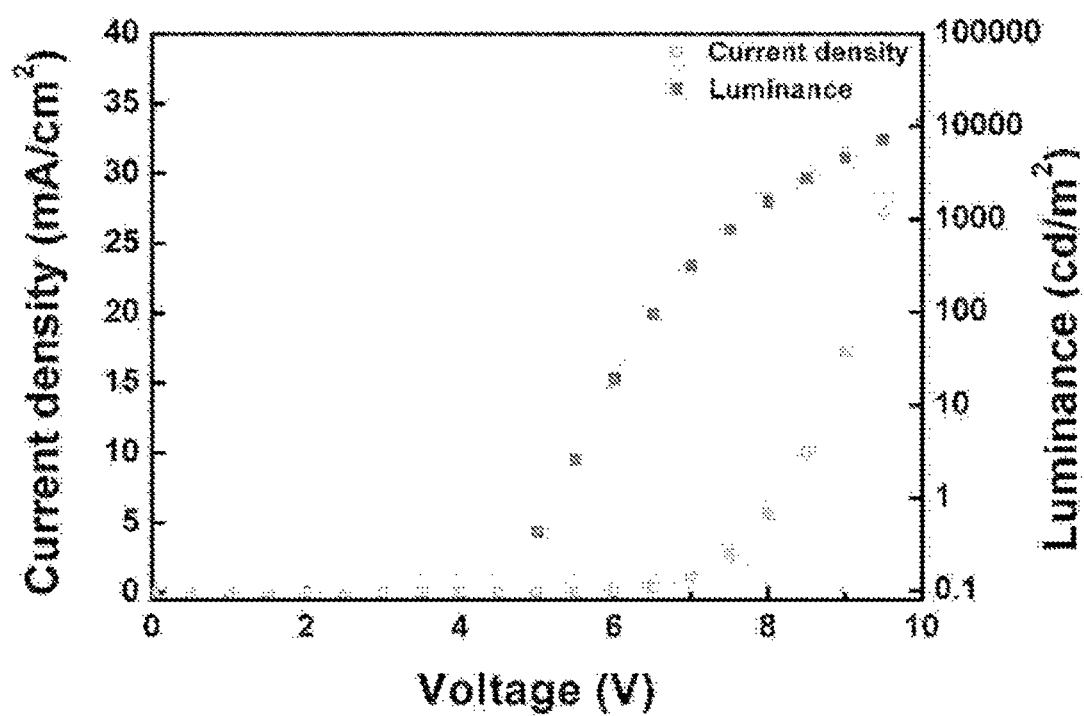
FIG. 2 is a graph showing current density and luminance according to voltage of a green phosphorescent OLED to which the compound according to various embodiments of the present disclosure is applied.

FIG. 2 is a graph showing current density and luminance according to voltage of a green phosphorescent OLED to which the compound according to various embodiments of the present disclosure is applied. According to various embodiments, the HBL 440 can block holes and transport electrons simultaneously. In the green phosphorescent OLED to which the compound according to various embodiments is applied to HBL 440, the ETL 450 used TPBi.

Table 2 below shows various characteristic values of the green phosphorescent OLED to which the compound according to various embodiments is applied to HBL 440.

TABLE 2

| Driving Voltage | Current Density | Luminance | Color coordinates | | Quantum efficiency (%) | | Power efficiency (lm/W) | | Current efficiency (Cd/A) | |
|---|---|---|---|---|---|---|---|---|---|---|
| (V) | (mA/cm$^2$) | (cd/m$^2$) | X | Y | [1000 cd] | [Max] | [1000 cd] | [Max] | [1000 cd] | [Max] |
| 7.7 | 3.6 | 1002.9 | 0.28 | 0.60 | 8.3 | 8.3 | 11.4 | 11.8 | 27.6 | 27.7 |

According to FIG. 2 and Table 2, when the compound according to various embodiments is applied to the HBL 440 of the green phosphorescent OLED, current density was 3.6 mA/cm$^2$, which is a significantly high value, at driving voltage of 7.7 V, indicating that the green phosphorescent OLED can be driven at a lower voltage. In addition, high luminance of 1002.9 cd/m$^2$ was observed at driving voltage of 7.7 V. Color coordinates were (0.27, 0.60) based on luminance of 1000 cd/m$^2$. Quantum efficiency, power efficiency and current efficiency were 8.3%, 11.4 lm/W and 27.6 Cd/A, respectively, based on luminance of 1000 cd/m$^2$, indicating high efficiency.

Figure 3:
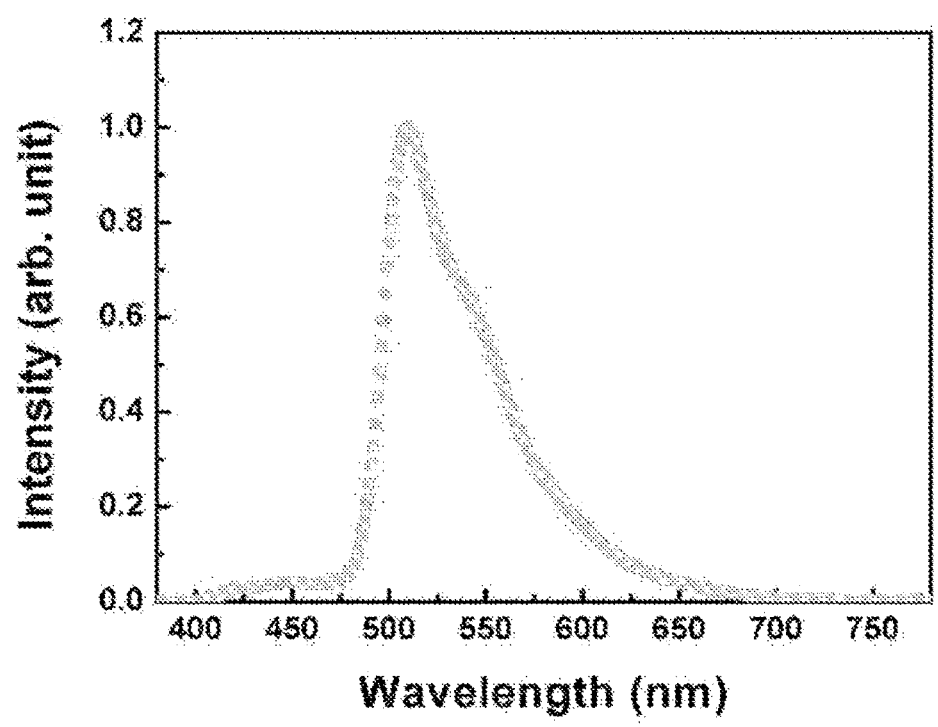
FIG. 3 is a graph showing an ElectroLuminescence (EL) spectrum of the green phosphorescent OLED to which the compound according to various embodiments of the present disclosure is applied.

FIG. 3 is a graph showing an ElectroLuminescence (EL) spectrum of the green phosphorescent OLED to which the compound according to various embodiments of the present disclosure is applied to HBL 440. The EL spectrum is a spectrum obtained by measuring light emitted from the OLED with a luminance meter.

As illustrated in FIG. 3, when the compound according to various embodiments is applied to the HBL 440 of the green phosphorescent OLED, it is observed that peak wavelength of the green EL spectrum is 500 nm to 520 nm and color purity is improved.

Figure 4:
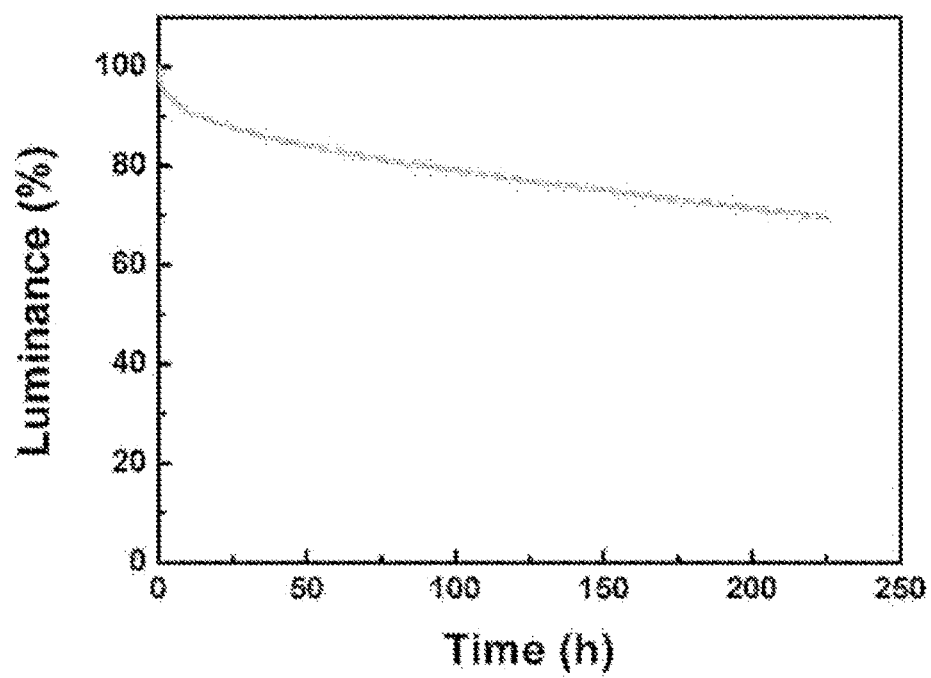
FIG. 4 is a graph showing changes in luminance over time of the green phosphorescent OLED to which the compound according to various embodiments of the present disclosure is applied.

FIG. 4 is a graph showing changes in luminance over time of the green phosphorescent OLED to which the compound according to various embodiments of the present disclosure is applied to HBL 440.

As illustrated in FIG. 4, in the case of the green phosphorescent OLED to which the compound according to various embodiments is applied, no significant change in luminance was observed over time. In other words, a long-life OLED could be obtained.

Figure 5:
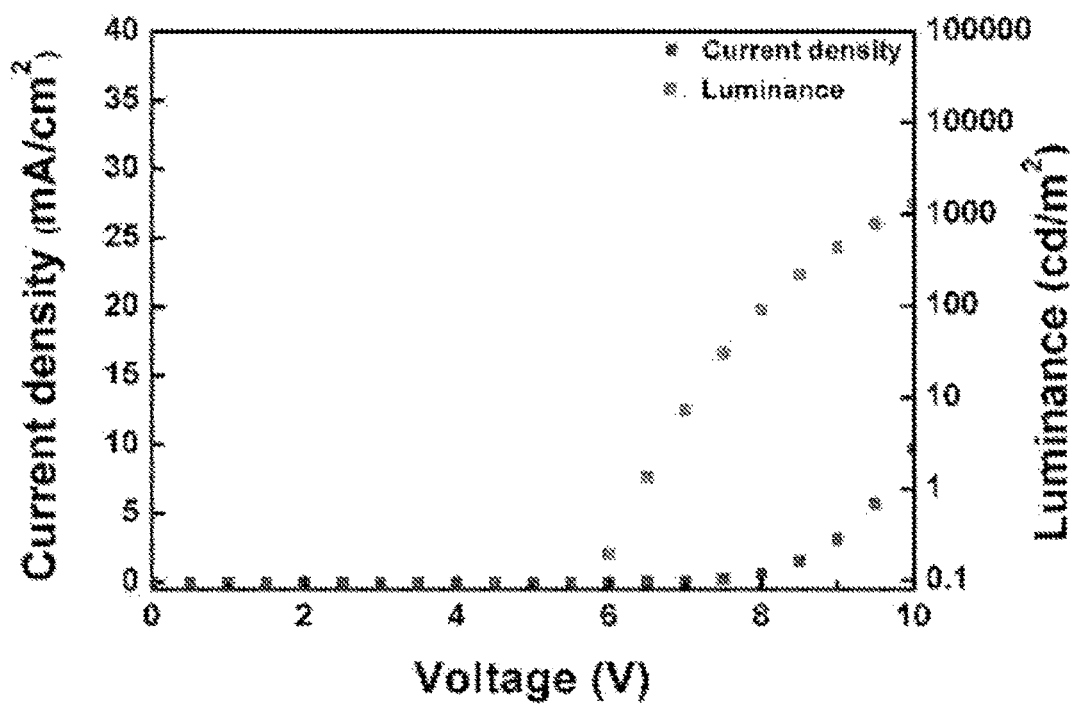
FIG. 5 is a graph showing current density and luminance according to voltage of a blue phosphorescent OLED to which the compound according to various embodiments of the present disclosure is applied.

FIG. 5 is a graph showing current density and luminance according to voltage of a blue phosphorescent OLED to which the compound according to various embodiments of the present disclosure is applied to HBL 440. According to various embodiments, the HBL 440 can block holes and transport electrons simultaneously. In the blue phosphorescent OLED to which the compound according to various embodiments is applied to HBL 440, the ETL 450 used LG 201 materials.

Table 3 below shows various characteristic values of the blue phosphorescent OLED to which the compound according to various embodiments is applied to HBL 440. The various characteristic values were measured by adjusting amounts of dopants in the EML 430 to 10%, 20% and 30%.

TABLE 3

| Dopant amount (%) | Driving Voltage (V) | Current Density (mA/cm$^2$) | Luminance cd/m$^2$) | Color coordinates X | Quantum efficiency (%) Y | Power efficiency (lm/W) [1000 cd] | Current efficiency (Cd/A) [Max] | Color coordinates X | Quantum efficiency (%) Y | Power efficiency (lm/W) [1000 cd] | Current efficiency (Cd/A) [Max] |
|---|---|---|---|---|---|---|---|---|---|---|---|
| 10 | 9.9 | 7.4 | 999.8 | 0.15 | 0.27 | 7.5 | 9.2 | 4.3 | 8.2 | 13.6 | 16.8 |
| 20 | 9.7 | 7.4 | 996.9 | 0.15 | 0.26 | 7.6 | 8.4 | 4.4 | 6.7 | 13.6 | 15.0 |
| 30 | 9.7 | 7.7 | 100.2 | 0.15 | 0.25 | 7.7 | 11.8 | 4.2 | 10.5 | 13.1 | 20.0 |

According to FIG. 5 and Table 3, when the compound according to various embodiments is applied to the HBL 440 of the blue phosphorescent OLED, if the amount of dopant in EML 430 was 30% and driving voltage is 9.7 V, current density was 3.6 mA/cm$^2$, which is a significantly high value, indicating that the blue phosphorescent OLED can be driven at a lower voltage. In addition, high luminance of 1002.2 cd/m$^2$ was observed at driving voltage of 9.7 V. Color coordinates were (0.15, 0.25) based on luminance of 1000 cd/m$^2$. Quantum efficiency, power efficiency and current efficiency were 7.2%, 4.2 lm/W and 13.1 Cd/A, respectively, based on luminance of 1000 cd/m$^2$, indicating high efficiency.

Figure 6:
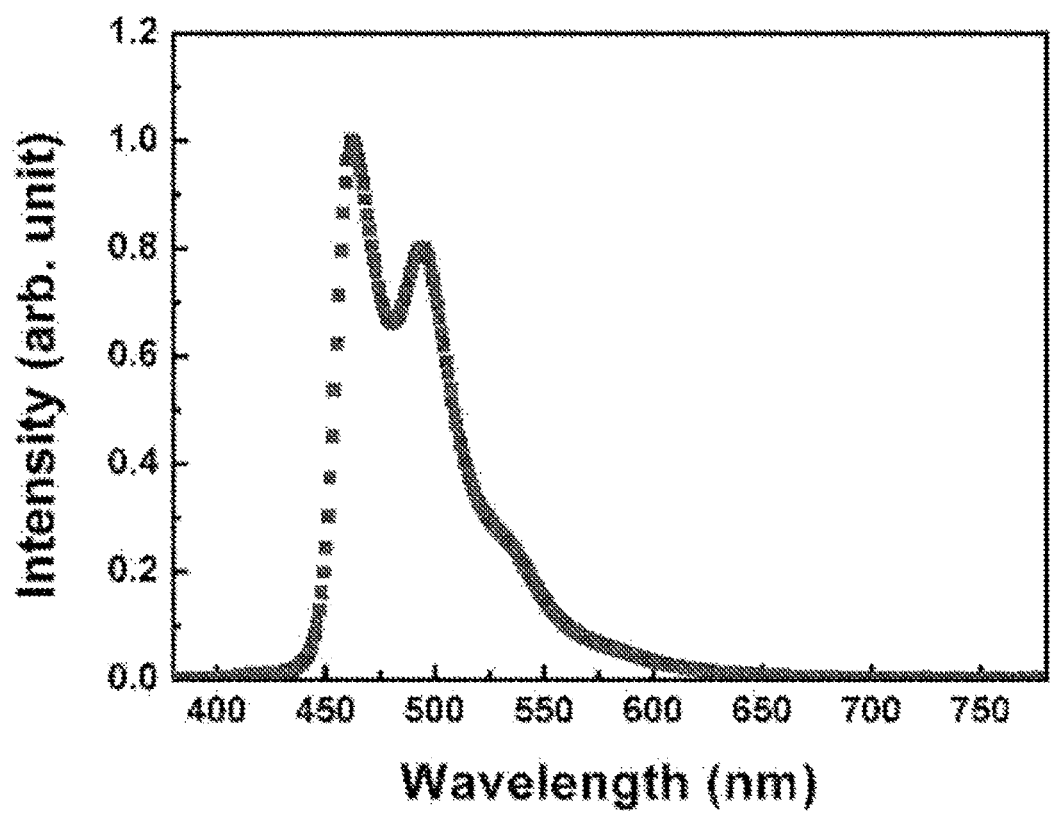
FIG. 6 is a graph showing an ElectroLuminescence (EL) spectrum of the blue phosphorescent OLED to which the compound according to various embodiments of the present disclosure is applied.

FIG. 6 is a graph showing an ElectroLuminescence (EL) spectrum of the blue phosphorescent OLED to which the compound according to various embodiments of the present disclosure is applied to HBL 440.

Figure 7:
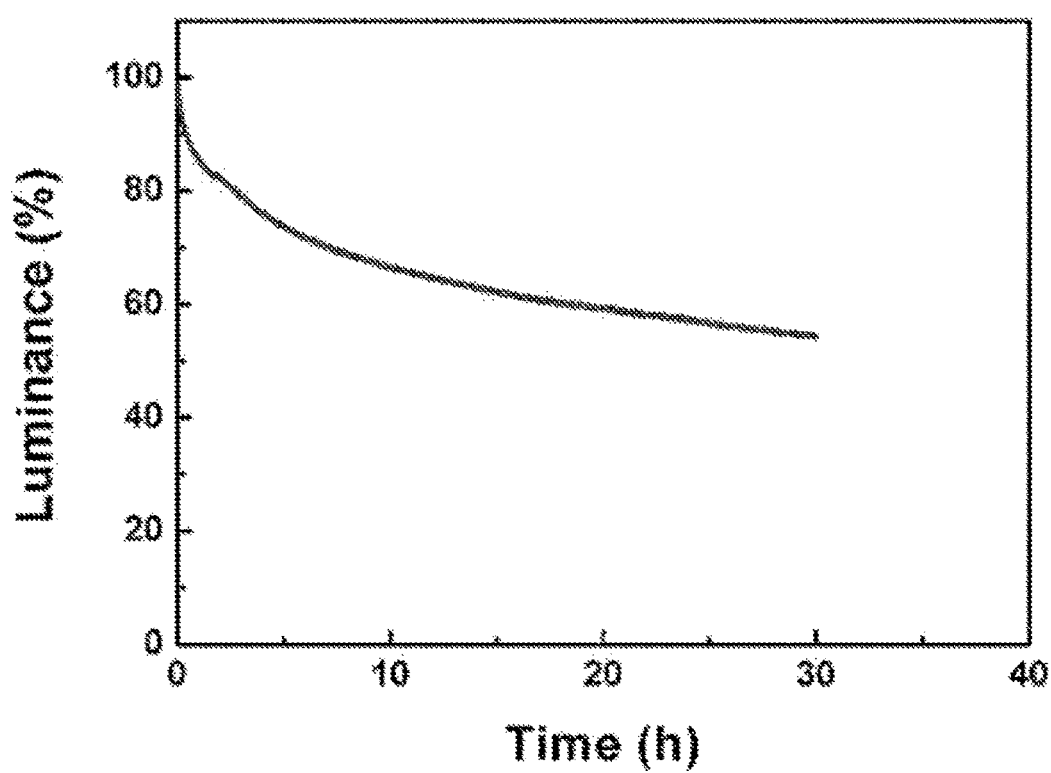
FIG. 7 is a graph showing changes in luminance over time of the blue phosphorescent OLED to which the compound according to various embodiments of the present disclosure is applied.

As illustrated in FIG. 6, when the compound according to various embodiments is applied to the HBL 440 of the blue phosphorescent OLED, it is observed that peak wavelength of the blue EL spectrum is 450 nm to 470 nm and color purity is improved FIG. 7 is a graph showing changes in luminance over time of the blue phosphorescent OLED to which the compound according to various embodiments of the present disclosure is applied to HBL 440.

As illustrated in FIG. 7, in the case of the blue phosphorescent OLED to which the compound according to various embodiments is applied, no significant change in luminance was observed over time. In other words, a long-life OLED could be obtained.

The features, structures, effects, and the like, which are described in the embodiments are included in at least one embodiment of the present disclosure and are not necessarily limited to one embodiment. Furthermore, the features, structures, effects, and the like illustrated in each embodiment can be combined and modified in other embodiments by those skilled in the art. Accordingly, the descriptions related to such combinations and modifications should be understood as being included in the scope of the present disclosure.

In addition, although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:
1. A compound of Formula 2 or Formula 3 below:

[Formula 2]

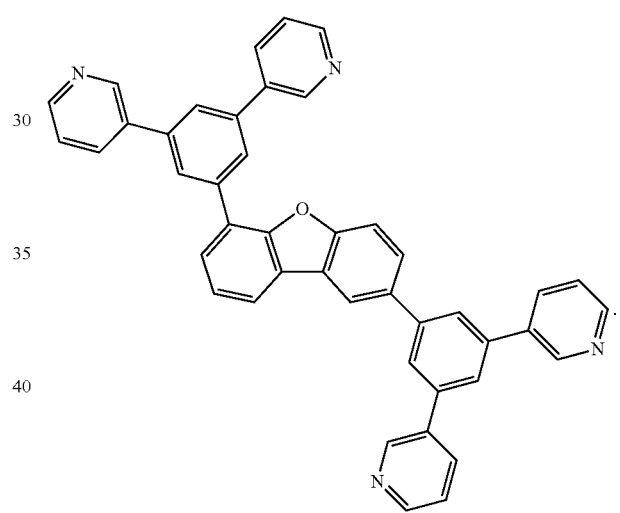

[Formula 3]

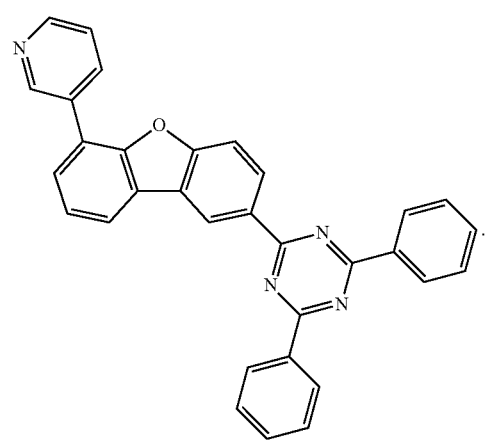

2. The compound of claim 1, wherein the compound is the compound of Formula 2.

3. An organic light-emitting diode, comprising:
   an anode;
   a cathode; and
   at least one organic thin film layer interposed between the anode and the cathode,
   wherein at least one layer of the organic thin film layers comprises a compound according to claim 2.

4. The compound of claim 1, wherein the compound is the compound of Formula 3.

5. An organic light-emitting diode, comprising:
   an anode;
   a cathode; and
   at least one organic thin film layer interposed between the anode and the cathode,
   wherein at least one layer of the organic thin film layers comprises a compound according to claim 4.

6. An organic light-emitting diode, comprising:
   an anode;
   a cathode; and
   at least one organic thin film layer interposed between the anode and the cathode,
   wherein at least one layer of the organic thin film layers comprises a compound according to claim 1.

7. The organic light-emitting diode of claim 6, wherein the organic thin film layer further comprises at least one selected from the group consisting of a hole injection layer (HIL), a hole transport layer (HTL), a hole blocking layer (HBL), an electron transport layer (ETL) and an electron injection layer (EIL).

8. A method for preparing a compound comprising:
   a process of synthesizing a compound of Formula 4 below by reacting 4-bromodibenzofuran, iodobenzene-diacetate and iodine:

[Formula 4]

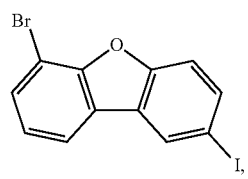

a process of synthesizing a compound of Formula 5 below by reacting pyridine-3-boronic acid, 1,3,5-tribromobenzene, sodium carbonate and tetrakis(triphenylphosphine)palladium:

[Formula 5]

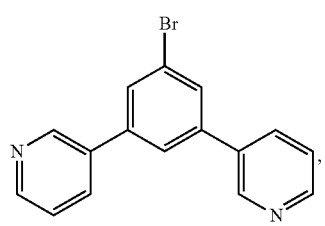

a process of synthesizing a compound of Formula 6 below by reacting the compound of Formula 5, bis(pinacolato)diboron, potassium acetate and [1,1'-bis(diphenylphosphino)ferrocene]dichloropalladium dichloromethane:

[Formula 6]

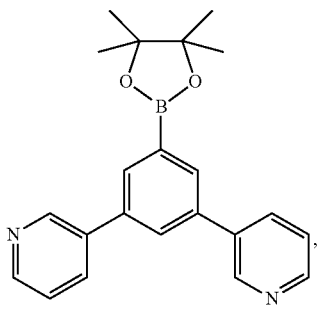

and
a process of synthesizing the compound of Formula 2 below by reacting the compounds of Formulae 4 and 6, potassium phosphate, tris(dibenzylidyneacetone)dipalladium and SPhos:

[Formula 2]

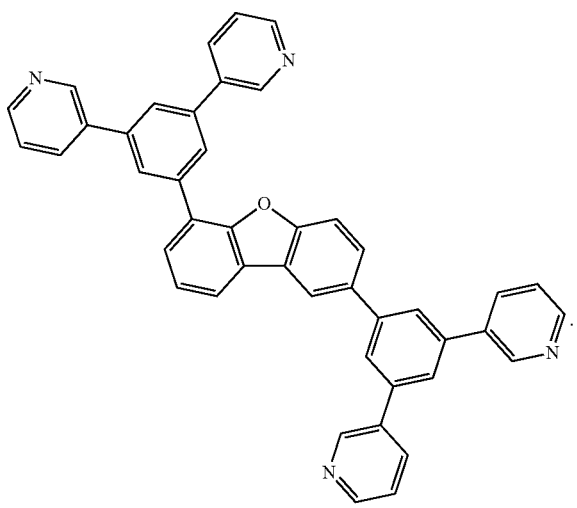

9. A method for preparing a compound comprising:
   a process of synthesizing a compound of Formula 4 below by reacting 4-bromodibenzofuran, iodobenzene-diacetate and iodine:

[Formula 4]

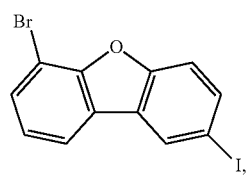

a process of synthesizing a compound of Formula 7 below by reacting the compound of Formula 4, bis(pinacolato)diboron, potassium acetate and [1,1'-bis(diphenylphosphino)ferrocene]dichloropalladium:

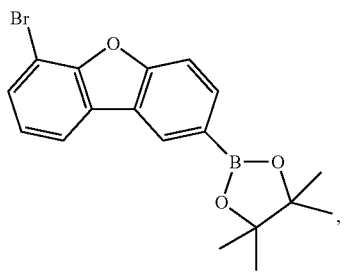

[Formula 7]

a process of synthesizing a compound of Formula 8 below by reacting magnesium, iodine, tetrahydrofuran, trichlorotriazine, and bromobenzene:

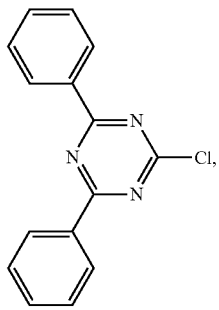

[Formula 8]

a process of synthesizing a compound of Formula 9 below by reacting the compounds of Formulae 7 and 8, sodium carbonate and tetrakis(triphenylphosphine)palladium:

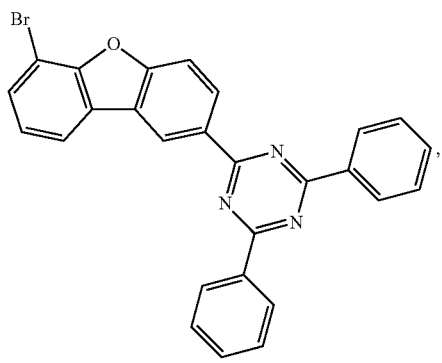

[Formula 9]

and a process of synthesizing the compound of Formula 3 below by reacting the compound of Formula 9, pyridine-3-boronic acid, potassium phosphate, tris(dibenzylidyneacetone)dipalladium and SPhos:

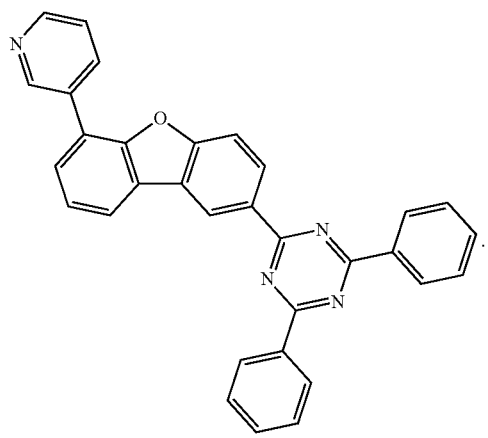

[Formula 3]

* * * * *